United States Patent
Karandikar et al.

(10) Patent No.: US 10,945,431 B2
(45) Date of Patent: *Mar. 16, 2021

(54) NON-STREAKING DURABLE COMPOSITION FOR CLEANING AND DISINFECTING HARD SURFACES

(71) Applicant: Ecolab USA Inc., Saint Paul, MN (US)

(72) Inventors: Yamini Karandikar, Saint Paul, MN (US); Mark Dennis Levitt, Saint Paul, MN (US); Joseph R. Wegner, Saint Paul, MN (US); Kim R. Solomon, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/548,558

(22) Filed: Aug. 22, 2019

(65) Prior Publication Data

US 2019/0373886 A1    Dec. 12, 2019

Related U.S. Application Data

(63) Continuation of application No. 15/207,132, filed on Jul. 11, 2016, now Pat. No. 10,433,545.

(51) Int. Cl.
| | | |
|---|---|---|
| *A01N 33/12* | (2006.01) | |
| *A01N 25/30* | (2006.01) | |
| *A01N 25/22* | (2006.01) | |
| *C11D 3/48* | (2006.01) | |
| *C11D 3/33* | (2006.01) | |
| *C11D 1/75* | (2006.01) | |
| *A61L 2/18* | (2006.01) | |
| *C11D 3/30* | (2006.01) | |

(52) U.S. Cl.
CPC ............. *A01N 33/12* (2013.01); *A01N 25/30* (2013.01); *A61L 2/18* (2013.01); *C11D 1/75* (2013.01); *C11D 3/30* (2013.01); *C11D 3/33* (2013.01); *C11D 3/48* (2013.01)

(58) Field of Classification Search
None
See application file for complete search history.

(56) References Cited

U.S. PATENT DOCUMENTS

| | | |
|---|---|---|
| 3,539,520 A | 11/1970 | Cantor et al. |
| 3,839,234 A | 10/1974 | Roscoe |
| 4,315,828 A | 2/1982 | Church |
| 4,343,725 A | 8/1982 | Kiewert et al. |
| 4,606,850 A | 8/1986 | Malik |
| 4,784,786 A | 11/1988 | Smith et al. |
| 4,971,631 A | 11/1990 | Sallee et al. |
| 5,008,030 A | 4/1991 | Cook et al. |
| 5,435,935 A | 7/1995 | Kupneski |
| 5,454,983 A | 10/1995 | Michael et al. |
| 5,454,984 A | 10/1995 | Graubart et al. |
| 5,547,900 A | 8/1996 | Hall et al. |
| 5,576,284 A | 11/1996 | van Buskirk et al. |
| 5,602,069 A | 2/1997 | Wisniewski et al. |
| 5,602,090 A | 2/1997 | Melikyan et al. |
| 5,646,105 A | 7/1997 | Hachmann et al. |
| 5,798,324 A | 8/1998 | Svoboda |
| 5,849,681 A | 12/1998 | Neumiller et al. |
| 5,929,016 A | 7/1999 | Harrison |
| 6,013,615 A | 1/2000 | Zhou et al. |
| 6,090,771 A | 7/2000 | Burt et al. |
| 6,121,224 A | 9/2000 | Fonsny et al. |
| 6,159,924 A | 12/2000 | Weller et al. |
| 6,255,270 B1 | 7/2001 | Barger et al. |
| 6,277,805 B1 | 8/2001 | Kupneski |
| 6,281,178 B1 | 8/2001 | Ryklin et al. |
| 6,281,182 B1 | 8/2001 | Leonard et al. |
| 6,339,056 B1 | 1/2002 | Like |
| 6,346,508 B1 | 2/2002 | Leonard et al. |
| 6,350,727 B1 | 2/2002 | Flower |
| 6,361,787 B1 | 3/2002 | Shaheen et al. |
| 6,559,116 B1 | 5/2003 | Godfroid et al. |
| 6,649,580 B2 | 11/2003 | Aszman et al. |
| 6,667,289 B2 | 12/2003 | Harrison et al. |
| 6,699,825 B2 | 3/2004 | Rees et al. |
| 6,881,711 B1 | 4/2005 | Gershun et al. |
| 6,939,840 B2 | 9/2005 | Lichtenberg et al. |
| 7,048,806 B2 | 5/2006 | Ochomogo et al. |
| 7,148,187 B1 | 12/2006 | Simon et al. |
| 7,414,017 B2 | 8/2008 | Kong et al. |
| 7,576,047 B2 | 8/2009 | Kilkenny et al. |
| 7,964,548 B2 | 6/2011 | Herdt et al. |
| 8,455,551 B2 | 6/2013 | Heisig et al. |
| 8,648,027 B2 | 2/2014 | Mitchell et al. |
| 9,185,908 B2 | 11/2015 | Krug et al. |
| 9,234,165 B2 | 1/2016 | Hope et al. |
| 2002/0155969 A1 | 10/2002 | Rees et al. |
| 2005/0153857 A1 | 7/2005 | Sherry et al. |
| 2005/0277573 A1 | 12/2005 | Lichtenberg et al. |
| 2006/0293201 A1 | 12/2006 | Simon et al. |
| 2006/0293202 A1 | 12/2006 | Cate et al. |
| 2007/0179079 A1 | 8/2007 | Kilkenny et al. |
| 2009/0285871 A1 | 11/2009 | Cunningham et al. |
| 2010/0101605 A1 | 4/2010 | Saint Victor |

(Continued)

FOREIGN PATENT DOCUMENTS

| | | |
|---|---|---|
| CN | 103013687 A | 4/2013 |
| EP | 0623669 B1 | 9/1994 |

(Continued)

OTHER PUBLICATIONS

Stephan, "AMoonyx® 10", pp. 1-2, 2012.

(Continued)

*Primary Examiner* — Kyung S Chang
(74) *Attorney, Agent, or Firm* — McKee, Voorhees & Sease, PLC

(57) ABSTRACT

The present invention relates to quaternary ammonium disinfecting cleaning compositions comprising a quaternary ammonium compound, an alkyl a polyglycoside with a CMC greater than 1000 ppm and a chelant. Beneficially, the compositions provide residual sanitizing efficacy without diminished performance and without scale formation when diluted with hard water. The compositions are suitable for inactivating and/or reducing infectious agents, particularly Norovirus, Adenovirus, and Polyomavirus.

13 Claims, No Drawings

(56) References Cited

U.S. PATENT DOCUMENTS

| | | |
|---|---|---|
| 2010/0216890 A1 | 8/2010 | Lichtenberg et al. |
| 2010/0240562 A1 | 9/2010 | Herdt et al. |

FOREIGN PATENT DOCUMENTS

| | | |
|---|---|---|
| EP | 0623669 A2 | 11/1994 |
| EP | 0728177 B1 | 8/1996 |
| EP | 0730629 B1 | 2/1999 |
| EP | 1148116 B1 | 10/2001 |
| EP | 1322156 B1 | 3/2006 |
| EP | 1671541 B1 | 4/2016 |
| GB | 2318585 A | 4/1998 |
| GB | 2374604 A | 10/2002 |
| GB | 2374604 B | 1/2003 |
| GB | 2475790 A | 6/2011 |
| JP | 2002517602 A | 6/2002 |
| JP | 2004161940 A | 6/2004 |
| JP | 2004162041 A | 6/2004 |
| JP | 2004285071 A | 10/2004 |
| JP | 2008266375 A | 11/2008 |
| JP | 4647912 B2 | 12/2010 |
| WO | 9405753 A1 | 3/1994 |
| WO | 9513345 A1 | 5/1995 |
| WO | 9729173 A1 | 8/1997 |
| WO | 9953009 A1 | 10/1999 |
| WO | 9964548 A1 | 12/1999 |
| WO | 0023553 A1 | 4/2000 |
| WO | 0155291 A1 | 8/2000 |
| WO | 0208372 A1 | 1/2002 |
| WO | 0223990 A1 | 3/2002 |
| WO | 2006027550 A1 | 3/2006 |
| WO | 2006114243 A1 | 11/2006 |
| WO | 2007001593 A1 | 1/2007 |
| WO | 2007001594 A2 | 1/2007 |
| WO | 2011064554 A1 | 6/2011 |
| WO | 2012090101 A2 | 7/2012 |
| WO | 2012090102 A2 | 7/2012 |
| WO | 2015078496 A1 | 6/2015 |

OTHER PUBLICATIONS

Ecolab USA, Inc., "Notification of Transmittal of the International Search Report and the Written Opinion of the International Searching Authority, or the Declaration", dated Sep. 25, 2017.

US 10,945,431 B2

NON-STREAKING DURABLE COMPOSITION FOR CLEANING AND DISINFECTING HARD SURFACES

CROSS REFERENCE TO RELATED APPLICATION

This is a Continuation Application of U.S. Ser. No. 15/207,132, filed Jul. 11, 2016, which is herein incorporated by reference in its entirety.

FIELD OF THE INVENTION

The present invention relates to multi-surface quaternary ammonium disinfectant cleaning compositions that are streak free, safe on marble, efficacious against Norovirus and provide residual sanitizing after application to the surface. The compositions of the present invention can be used for cleaning and disinfecting surfaces in one step combining antimicrobial efficacy with short contact times.

BACKGROUND OF THE INVENTION

Microbes may often be present on many common objects and surfaces in everyday life. Examples include, for example, bacteria, fungi, spores, viruses, prions, microorganisms such as, e.g., *Mycobacterium tuberculosis, Listeria monocytogenas, Escherichia coli, Pseudomonas aeruginosa, Salmonella typhimurium, Salmonella enteritidis, Yersinia pestis, Staphylococcus aureus, Bacillus subtilis, Enterobacter aerogenes, Streptococcus faecalis, Legionella pneumophila, Vibrio parahaemolyticus, Bacillus cereus*, and other gram positive and gram negative bacteria. Several such microbes/microorganisms, individually or in combination, can cause illness or other health problems, for example, when they come into contact with humans and/or animals, or when they are ingested along with food which has contacted them. These microbes present health hazards due to infection or contamination.

Public and private facilities such as, e.g., restrooms, may also contain surfaces which can harbor and spread microbes, leading to potential health problems. To address this issue, products such as antimicrobial soaps and air dryers for hands may be offered, as well as disposable paper towels. Nevertheless, microbes may still be harbored on such objects as faucet and toilet handles, door knobs, keys, dispenser levers, etc.

In the transportation industry, including land, sea, air, and space vehicles, there may also be particular surfaces which can harbor and spread microbes, leading to potential health problems. For example, rental cars may benefit from durable antimicrobial surfaces (both interior and exterior). In particular, isolated environments such as, e.g., airplanes and submarines can also be safer if provided with antimicrobial surfaces.

Other common objects may benefit from antimicrobial compositions, which can inhibit or prevent spread of microorganisms between people and/or animals that come into contact with such objects. For example, musical instruments, such as harmonicas, flutes, clarinets, etc., computer peripherals, communications equipment such as, e.g., telephones, pet accessories such as leashes and carriers, and/or other common household objects could benefit from anti-microbial surfaces.

One can see that there is a continuing need for improved antimicrobial cleanings, coatings, and sanitizers which are durable and effective in rapid and high level killing or inhibiting growth of microbes such as bacteria and other microorganisms.

There is a need to provide such materials and coatings which are easy and relatively inexpensive to produce, which have a long life time of killing, which do not wear off easily, and which may be applied to a broad variety of substrates.

In addition, there is a need for such antimicrobial coatings which can be applied to objects that are already in use (clean in place) or that are in need of repair.

While most currently available sanitizers and disinfectants provide immediate kill properties when contaminated surfaces are exposed to the antimicrobial agent for the specified contact time, there is no assurance that the surface will remain safe for use. In fact, the next time a contaminated object, animate or inanimate, touches the surface it may be re-contaminated. Therefor there remains a need for a product capable of enabling continued germicidal efficacy. Also, in janitorial and building maintenance cleaning there is a material advantage to reducing the number of products that are needed for cleaning and disinfecting. Reducing the number of cleaning products simplifies training, use, storage, etc. The ability to combine a glass cleaner and disinfectant cleaner eliminates the need for at least one product. However many germicidal cleaners are not acceptable for this purpose as they leave an unsightly streaky residue after cleaning.

Also, it is known that one of the main sources of food poisoning is the norovirus. Norovirus is particularly onerous in the long-term care environment, food service and cruise ship industries. Norovirus is an unenveloped virus. Unenveloped viruses are well known to be more difficult to kill than enveloped viruses and many vegetative bacteria. Norovirus is particularly resistant to inactivation by certain antimicrobial agents including quaternary ammonium chlorides.

There remains a need for a germicidal cleaner that possesses a multiplicity of performance properties including disinfection, virucidal efficacy, glass cleaning performance and residual sanitizing. While any one or two of these properties can be achieved using known formulation means, combining all of the properties is not difficult for many reasons including the fact that certain ingredients that may enable one property may act antagonistically to another property. For example, it is known that amine oxide surfactants can enable glass cleaning performance, they tend to diminish certain biocidal properties. Organic solvents may act to improve certain properties, but there is a need to minimize the use of volatile organic solvents to reduce smog formation in urban environments.

The present invention provides anti-microbial compositions which address one or more of the aforementioned needs as well as others which will become apparent form the description of the invention which follows.

BRIEF SUMMARY OF THE INVENTION

Applicants have developed a quaternary ammonium chloride based multi-surface five minute disinfectant cleaning that is streak-free on reflective surfaces, demonstrates virucidal efficacy against norovirus and is safe on marble. This product also has residual chemistry and will continue to sanitize surfaces for 24 hours after initial application. Surprisingly according to the invention, the streak-free chemistry does not require the use of a solvent. The chemistry uses a unimer quaternary ammonium compound along with two or more co-surfactants including a C12 or higher diethyl, or dimethyl amine oxide and an alkyl polyglycoside having a high critical micelle concentration (CMC) which act synergistically to achieve the desired properties.

The present invention is directed to a disinfectant surface cleaning composition comprising at least one biocidal quaternary ammonium compound; in combination with a alkyl polyglycoside and an amine oxide co-surfactant where the alkyl polyclycoside has a CMC of 1000 or higher and the amine oxide has a CMC higher than the quaternary ammonium compound. The composition preferably has a ratio difference in CMC between the co-surfactant and quaternary ammonium compound of at least about 2×. The invention includes an alkyl polyglycoside with a CMC greater than 1000. The invention also includes a second co-surfactant of an amine oxide surfactant with a carbon chain of C12 or higher. The composition can also include a water hardness control agent/chelating agent, preferably EDTA, and may further include in certain embodiments an additional antimicrobial or synergist such as an amine.

In a preferred embodiment that quaternary ammonium compound is a dialkyl quaternary ammonium compound, and is free of benzyl or aromatic quaternary substituents, such as ADBAC. In a surprising and unexpected feature of the invention the Composition is free of many agents typically found in such cleanings including: solvents volatile or nonvolatile, ethanol, benzyl alcohols, glycol ethers, and glycerin. Surprisingly, applicants have provided a composition without these components which is not only streak free, but which also provides superior cleaning with residual antibacterial activity. In certain embodiments, the composition is active against virus as well as gram-negative Enterobacteriaceae such as *Salmonella, Escherichia coli, Yersinia pestis, Klebsiella* and *Shigella*.

The disinfectant cleaning composition of the invention can be used for inactivating and/or reducing infectious agents, comprising bacteria, virus, and/or yeasts, on hard and/or soft surfaces. In particular, the disinfectant cleaning composition of the invention can be used for activating and/or reducing virus, including unenveloped viruses on hard and/or soft surfaces, such as Adenovirus and/or Norovirus and/or viruses of the Polyomavirus and/or Papillomavirus-group. These compositions provide excellent cleaning and disinfecting of a hard surface while leaving no visible residue or streaks.

DETAILED DESCRIPTION OF THE PREFERRED EMBODIMENT

It is to be understood that all terminology used herein is for the purpose of describing particular embodiments only, and is not intended to be limiting in any manner or scope. For example, as used in this specification and the appended claims, the singular forms "a," "an," and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range. So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about," the claims include equivalents to the quantities.

As used herein, the term "free" refers to compositions completely lacking the component or having such a small amount of the component that the component does not affect the effectiveness of the composition. The component may be present as an impurity or as a contaminant or present in small amounts in a commercial formulation of components used in the composition for various reasons, but in any event the component shall be less than 0.5 wt. %.

The term "actives" or "percent actives" or "percent by weight actives" or "actives concentration" are used interchangeably herein and refers to the concentration of those ingredients involved in cleansing expressed as a percentage minus inert ingredients such as water or salts. Note that percentages reported in the examples section only are total percentages of components as received from commercial vendors and in those tables, do include inert ingredients such as water or salts.

As used herein, the term "substantially free" refers to compositions completely lacking the component or having such a small amount of the component that the component does not affect the performance of the composition. The component may be present as a minor constituent and/or impurity or contaminant and shall be less than 5 wt-%. In another embodiment, the amount of the component is less than 1 wt-% and in yet another embodiment, the amount of component is less than 0.1 wt-%. For example, the composition may include commercially available quaternary ammonium chloride surfactants. These surfactants are commonly sold in concentrations of 50% or 80%. The product of trade will typically contain up to 10% alcohol to aid in stability. If the commercially available quat product is used in the disinfectant composition at 35%, there may be as much as 3.5% alcohol as an incidental addition. This alcohol is not needed to provide any needed properties of the composition and is only present incidentally.

The term Multi-Surface Cleaner means a hard surface cleaner that removes normal household type soils from a variety of surfaces including glass. To achieve this performance, it must not leave streaks or unsightly residues on the glass after cleaning.

As used herein, weight percent "wt-%," "percent by weight," "% by weight," and variations thereof refer to a composition, component, substance or agent as the weight of that composition, component, substance or agent of the disinfectant cleaning composition divided by the total weight of the disinfectant cleaning composition or use composition and multiplied by 100. It is understood that the total weight percent amount of all components, substances or agents of the disinfectant cleaning composition as well as use composition are selected such that it does not exceed 100 wt.-%.

It is understood that, as used here, "percent," "%", and the like are intended to be synonymous with "weight percent," "wt-%," etc.

As used herein the term critical micelle concentration (CMC) is stated in units of ppm and measured in water at a temperature of 20 to 25 degrees C. It is generally defined as the concentration of the surfactant in question above which micelles form.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, the term "disinfectant" refers to an agent that kills all vegetative cells including most recognized pathogenic microorganisms, using any scientifically accepted procedure such as a procedure approved by the Environmental Protection Agency (EPA), including the AOAC Use Dilution Method for Testing Disinfectants (Method ID MB-05-13), the Germicidal Spray Procedures as Disinfectants (Method ID MB-06-08), Disinfectant Towlette Test Method ID MB-09-06.

As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital, broad spectrum, or limited-spectrum disinfectant by the EPA.

As used herein, the term "hard surface" includes showers, sinks, toilets, bathtubs, countertops, windows, mirrors, transportation vehicles, floors, and the like. These surfaces can be those typified as "hard surfaces" (such as walls, floors, bed-pans, etc.).

As used herein, the phrase "health care surface" refers to a surface that normally contacts intact skin, including a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term virucide, or virucidal means it is capable of passing scientifically acknowledged test for the same, for example a US EPA approved test method for virucidal efficacy in force at the time of the application. Preferably the test method is ASTM E1053-11.

As used herein, the term "sanitizer" refers to an agent that reduces the number of bacterial contaminants to safe levels as judged by public health requirements. In an embodiment, sanitizers for use in this invention will provide at least a 99.9% reduction (3-log order reduction). These reductions can be evaluated using a procedure set out in ASTM E-1153).

The term "solvent" refers to an organic material or mixture of such materials suitable for cleaning, degreasing or stripping the desired surface, coupling, coalescing or adjusting viscosity.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

The germicidal test methods referred to are those approved by the EPA for germicide registration in force at the time of the patent application. *Staphylococcus aureus* is the ATCC 6538 strain.

The methods and compositions of the present invention may comprise, consist essentially of, or consist of the components/ingredients and steps set forth for the present invention as well as other ingredients and/or production steps described herein. As used herein, "consisting essentially of" means that the methods and compositions may include additional steps, components or ingredients, but only if the additional steps, components or ingredients do not materially alter the basic and novel characteristics of the claimed methods and compositions.

Disinfectant Composition

According to one embodiment of the invention, the disinfectant cleaning composition may comprise:
a unimer quaternary ammonium compound; an amine oxide co-surfactant of C12 or higher;
a glycoside co-surfactant exhibiting a of CMC 1000 or higher, a chelant, and an optional additional antimicrobial agent or synergist such as an amine.

Biocidal Quaternary Ammonium Compounds

The disinfectant cleaning composition of the invention may comprise at least one biocidal quaternary ammonium compound. The biocidal quaternary ammonium compound is useful as a disinfectant. Quaternary ammonium compounds, also known as "quats", typically comprise at least one quaternary ammonium cation with an appropriate anion. The quaternary ammonium cations are permanently charged, independent of the pH of their solution.

The structure of the cation can be represented as follows:

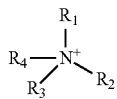

The groups $R_1$, $R_2$, $R_3$ and $R_4$ can vary within wide limits and examples of quaternary ammonium compounds that have anti-microbial properties will be well known to the person of ordinary skill in the art.

Each group $R_1$, $R_2$, $R_3$ and $R_4$ may, for example, independently be a substituted or unsubstituted and/or straight chain or branched and/or interrupted or uninterrupted alkyl, aryl, alkylaryl, arylalkyl, cycloalkyl, (aromatic or non-aromatic) heterocyclyl or alkenyl group. Alternatively, two or more of $R_1$, $R_2$, $R_3$ and $R_4$ may together with the nitrogen atom form a substituted or unsubstituted heterocyclic ring. The total number of carbon atoms in the groups $R_1$, $R_2$, $R_3$ and $R_4$ must be at least 4. Typically the sum of the carbon atoms in the groups $R_1$, $R_2$, $R_3$ and $R_4$ is 10 or more. In a preferred aspect of the invention at least one of the groups $R_1$, $R_2$, $R_3$ and $R_4$ contains from 8 to 18 carbon atoms. For example, 1, 2, 3 or 4 of $R_1$, $R_2$, $R_3$ and $R_4$ can contain from 8 to 18 carbon atoms or 10 to 16 carbon atoms.

Suitable substituents for the groups $R_1$, $R_2$, $R_3$ and $R_4$ may be selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, —OR¹, —NR¹R", —CF₃, —CN, —NO₂, —C₂R¹, —SR', —N₃, —C(=O)NR'R", —NR¹C(O)R", —C(=O)R\ —C(=O)OR\ —OC(O)R¹, —O(CR'R$^x$),C(=O)R', O(CR'R"),NR"C(O)R', —O(CR'R"), NR"SO₂R', —OC(O)NR¹R", —NR¹C(O) OR", —SO₂R', —SO₂NR¹R", and —NR¹SO₂R", wherein $R^1$ and R" are individually hydrogen, $C_1$-$C_8$ alkyl, cycloalkyl, heterocyclyl, aryl, or arylalkyl, and r is an integer from 1 to 6, or R' and R" together form a cyclic functionality, wherein the term "substituted" as applied to alkyl, alkenyl, heterocyclyl, cycloalkyl, aryl, alkylaryl and arylalkyl refers to the substituents described above, starting with F and ending with —NR¹SO₂R".

When one or more of $R_1$, $R_2$, $R_3$ and $R_4$ is interrupted, suitable interrupting groups include but are not limited to heteroatoms such as oxygen, nitrogen, sulphur, and phosphorus-containing moieties (e.g. phosphinate). A preferred interrupting group is oxygen.

Suitable anions for the quats include but are not limited to halide anions such as chloride, fluoride, bromide or iodide and the non-halide sulphonate, ethosulfate, salicylic acid, carbonate, bicarbonate, etc.

Some examples of quats include those having the formula: $(CH_3)_n(A)_m N^+ X^-$ wherein A may be as defined above in relation to $R_1$, $R_2$, $R_3$ and $R_4$. X" is selected from chloride, fluoride, bromide or iodide and sulphonate (preferably chloride or bromide), n is from 1 to 3 (preferably 2 or 3) and m is from 1 to 3 (preferably 1 or 2) provided that the sum of n and m is 4. Preferably, A is a $C_{6-20}$ (e.g. $C_{8-18}$, i.e. having 8, 9, 10, 11, 12, 13, 14, 15, 16, 17 or 18 carbon atoms or $C_{8-12}$ or $C_{12-18}$) substituted or unsubstituted and/or straight chain or branched and/or interrupted or uninterrupted alkyl, aryl, alkylaryl, arylalkyl or cycloalkyl group (wherein suitable substituents are as defined above in relation to $R_1$, $R_2$, $R_3$ and $R_4$). Each group A may be the same or different.

Another group of the compounds of formula $(CH_3)_n(A)_m N^+ X'$ are those wherein n=3 and m=1. In such compounds A may be as defined above and is preferably a $C_{6-20}$ substituted or unsubstituted and/or straight chain or branched and/or interrupted or uninterrupted alkyl, aryl, or alkylaryl group. Examples of this type of quaternary ammonium compound include Cetrimide (which is predominately trimethyltetradecylammonium bromide), dodecyltrimethylammonium bromide, trimethyltetradecylammonium bromide, hexadecyltrimethylammonium bromide.

Another preferred group of the compounds of formula $(CH_3)_n(A)_m N^+ X'$ are those wherein n=2 and m=2. In such compounds A may be as defined above in relation to $R_1$, $R_2$, $R_3$ and $R_4$. Preferably A is a $C_{6-20}$ substituted or unsubstituted and/or straight chain or branched and/or interrupted or uninterrupted alkyl, aryl, or alkylaryl group. For example, A may represent a straight chain, unsubstituted and uninterrupted $C_{8-12}$ alkyl group or a benzyl group. In these compounds, the groups A may be the same or different. Examples of this type of compound include didecyl dimethyl ammonium chloride, octyl decyl dimethyl ammonium chloride, and dioctyl dimethyl ammonium chloride.

Some examples of quaternary ammonium compounds described above include the group of compounds which are generally called benzalkonium halides and aryl ring substituted derivatives thereof. Examples of compounds of this type include benzalkonium chloride, which has the structural formula:

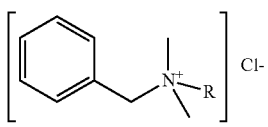

wherein R may be as defined above in relation to $R_1$, $R_2$, $R_3$ and $R_4$. Preferably, R is a $C_{8-18}$ alkyl group or the benzalkonium chloride is provided and/or used as a mixture of $C_8$-is alkyl groups, particularly a mixture of straight chain, unsubstituted and uninterrupted alkyl groups n-$C_8H_{17}$ to n-$C_{18}H_{37}$, e.g. n-$Ci_2H_25$ to n $C_{18}H_{37}$ mainly n-$C_{12}H_{25}$ (dodecyl), n-$C_{14}H_{29}$ (tetradecyl), and n-$C_{16}H_{33}$ (hexadecyl).

Other quaternary ammonium compounds include those in which the benzene ring is substituted, for example alkyldimethyl ethylbenzyl ammonium chloride. As an example, a mixture containing, for example, equal molar amounts of alkyl dimethyl benzyl ammonium chloride and alkyldimethyl ethylbenzyl ammonium chloride may be used.

Other quaternary ammonium compounds suitable for use in the invention include, but are not limited to, alkylpyridinium compounds, such as cetylpyridinium chloride, and bridged cyclic amino compounds such as the hexaminium compounds.

The biocidal quaternary ammonium compound can be a quaternary ammonium chloride of N-alkyl dimethyl benzyl ammonium chloride. The N-alkyl dimethyl benzyl ammonium chloride, wherein said alkyl has from about 8 to about 18 carbon atoms, also known as benzalkonium chloride and ADBAC, is a cationic surface-acting agent belonging to the quaternary ammonium group. It has three main categories of use: as a biocide, a cationic surfactant, and phase transfer agent in the chemical industry.

The quaternary ammonium chloride can be: at least one N-alkyl dimethyl benzyl ammonium chloride, wherein said alkyl has from about 8 to about 18 carbon atoms, can be selected from the group of at least one alkyl(C14) dimethyl benzyl ammonium chloride, alkyl(C16) dimethyl benzyl ammonium chloride, alkyl(C18) dimethyl benzyl ammonium chloride, a mixture of N-alkyl(C8-C18) dimethyl benzyl ammonium chloride, or a mixture of N-alkyl(C10-C18) dimethyl benzyl ammonium chloride, or any combination thereof; and more preferred a N-alkyl(C10-C18) dimethyl benzyl ammonium chloride mixture, further preferred dodecyl dimethyl benzyl ammonium chloride and most preferred a N-alkyl(C10-C18) dimethyl benzyl ammonium chloride mixture. An exemplary N-alkyl(C10-C18) dimethyl benzyl ammonium chloride mixture is Barquat DM-50, produced by Lonza (Basel, Switzerland).

Preferred quaternary ammonium compounds useful for the invention include unimer quaternary compounds. The composition is preferably free of polymer quaternary ammonium compounds. Preferred quaternary ammonium compounds include a dialkyl quaternary ammonium compound, and the composition is preferably free of benzyl or aromatic substituents as described above. Applicants have surprisingly found that dialkyl quats which are less water soluble may be used according to the invention with appropriate co-surfactants which optimize disinfecting capabilities.

A preferred quaternary ammonium chloride is a blend of di-C8, C8C10 and di-C10 alkyl dimethyl ammonium chlorides. This blend is commercially available from Lonza Inc, Fair Lawn N.J. as Bardac 2050 (50% active) or Bardac 2080 (80% active). The individual componants of the blend are also available as Bardac LF, Bardac 2250 and Bardac 2280. The DiC8 and DiC10 dimethyl quats can be purchased as the aforementioned blend, or blended in-situ to make the desired ratio, which may not be the same ratio as the commercially available product, Bardac 2050. The quaternary ammonium chloride is also available from the Stepan Company, Northfield Ill., or the Pilot Chemical Company, Cincinnati Ohio.

A disinfectant cleaning composition of the invention, preferably in form of a concentrate, may comprise about 3000 to about 50; preferably 2500-300 ppm; and more preferably from about 1700-500 ppm in the use solution of a biocidal quaternary ammonium compound. On a weight percent basis, the concentrate can be from about 40.0 wt. % to about 0.7 wt. %; preferably from about 33.3 wt. % to about 6.7 wt. %; and most preferably from about 22.7 wt. % to about 3 wt. % of a biocidal quaternary ammonium compound.

A diluted disinfectant cleaning composition of the invention may comprise about 0.0001 wt.-% to about 3 wt.-%, preferably about 0.0005 wt.-% to about 2 wt.-%, more preferred about 0.001 wt.-% to about 1 wt.-%, and most preferred of about 0.005 wt.-% to about 0.5 wt.-% of a biocidal quaternary ammonium compound Alkyl Polyglycoside The composition of the invention include a non-functionalized alkyl polyglycoside (APG). Preferred APGs include alkyl polyglucosides, which are characterized by the saccharide moiety being glucose. Preferred alkyl polyglucosides have naturally derived glucoside groups.

The alkyl polyglycosides, which can be used in the present invention, are fatty ether derivatives of saccharides or polysaccharides which are formed when a carbohydrate is reacted under acidic condition with a fatty alcohol through condensation polymerization. The APGs commonly are derived from corn-based carbohydrates and fatty alcohols from natural oils in animals, coconuts and palm kernels. Natural gas, or petroleum based alcohols may also be used, particularly in shorter chain lengths. Such methods of deriving APGs are known in the art, for example, U.S. Pat. No. 5,003,057 (McCurry), and the description therein on the methods of making glycosides and chemical properties are incorporated by reference herein.

The alkyl polyglycoside that can be used in the present invention contains a hydrophilic group derived from carbohydrates and is composed of one or more anhydroglucose. Each of the glucose units can have two ether oxygens and three hydroxyl groups and a terminal hydroxyl group, imparting water solubility to the glycoside. The presence of the alkyl carbons leads to the hydrophobic activity. When carbohydrate molecules react with fatty alcohol molecules, alkyl polyglycoside molecules are formed with single or multiple anhydroglucose units, which are termed monoglycosides and polyglycosides, respectively. The final alkyl polyglycoside product typically has a distribution of varying concentration of glucose units (or degree of polymerization).

The APG used in the invention preferably comprises the saccharide or polysaccharide groups (i.e., mono-, di-, tri-, etc. saccharides) of hexose or pentose, and a fatty aliphatic group with 6 to 20 carbon atoms. Alkyl polyglycosides which can be used in the present invention are represented by the general formula of

where G is a moiety derived from a reducing saccharide containing 5 or 6 carbon atoms, e.g., pentose or hexose; R is fatty aliphatic group containing 6 to 20 carbon atoms; and x is the degree of polymerization (D.P.) of the polyglycoside, representing the number of monosaccharide repeating units in the polyglycoside. Generally, x is an integer on the basis of individual molecules, but because there are statistical variations in the manufacturing process of the APG, x may be a noninteger on an average basis when referred to APG used as an ingredient for the hard surface cleaning of the present invention. In this invention, x preferably has a value of less than about 5, and more preferably between about 0.5 and about 5. Even more preferably, x is less than about 2.5, and more preferably is within the range between about 1 and about 2.

Many commercially available alkyl polyglycosides may contain a blend of carbon lengths. Suitable alkyl polyglycosides include alkyl polyglycosides containing short chain carbons, such as chain lengths of less than $C_{16}$. In one example, suitable alkyl polyglycosides include $C_8$-$C_{16}$ alkyl polyglycosides. Additional description of suitable alkyl polyglycosides are set forth, for example, in U.S. Pat. Nos. 8,287,659 and 8,299,009, and U.S. patent application Ser. Nos. 12/819,667, 12/884,638, 12/887,716, 13/597,380, 13/622,392, and 13/653,965, which are herein incorporated by reference in their entirety.

Exemplary saccharides from which G is derived are glucose, fructose, mannose, galactose, talose, gulose, allose, altrose, idose, arabinose, xylose, lyxose and ribose. Because of the ready availability of glucose, glucose is preferred in the making of polyglycosides. The fatty aliphatic group, which is the substituent of the preferred polyglycoside, is preferably saturated, although unsaturated fatty group may be used.

In some embodiments the APGs have an average degree of polymerization of saccharides from 1.4 to 1.7 and the chain lengths of the aliphatic groups are between $C_{8-16}$. The alkyl polyglycosides suitable for this invention will be described as illustrated in the following way: "$C_{8-16}$ G 1.6" denotes a polyglycoside with an alkyl chain of 8 to 16 carbon atoms and an average degree of polymerization of 1.6 anhydroglucose units in the alkyl polyglucoside molecule. Commercially, alkyl polyglycosides can be provided as concentrated, aqueous solutions ranging from 50 to 70 wt. % active. Examples of commercial suppliers of alkyl polyglycosides are Dow, BASF, Seppic, Akzo Nobel, and Croda.

Functionalized APGs may also be included, with cationic, amphoteric, or anionic functional groups. Preferred fatty alcohol based alkyl polyglycosides exhibit CMCs greater than that of the quat component. Typically this preferably includes values of higher than 1000, preferably higher than 4000. According to the invention Applicants have discovered that high CMC APGs (at least CMC of 1000 or higher) work well with the active ingredient in the invention. While not wishing to be bound by any theory, high CMC APGs enable the quaternary ammonium chloride active ingredient to perform its biocidal function, allowing a fast, high kill without a high amount of active present. Low CMC surfactants (CMC below 1000) interfere with the active ingredient and reduce biocidal efficacy. Alkyl polyglycoside surfactants that have this level of CMC are typically those that have carbon chain lengths of predominantly 8 carbons or lower. It may, however, be possible to envision a longer chain APG which, by virtue of modification to the alkyl chain, such as branching, or substitution, demonstrates the desired high CMC.

A list of typical surfactants and their CMC values is below:

| Company | Trade name | Chain length | CMC (ppm) |
|---|---|---|---|
| BASF | Glucopon 215 UP | C8-C10 | 200 |
| BASF | Glucopon 225 DK | C8-C10 | 250 |
| BASF | Glucopon 325N | C9-C11 | 280 |
| BASF | Glucopon 420UP | C8-C14 | 50 |
| BASF | Glucopon 425N | C8-C14 | 50 |
| BASF | Glucopon 600UP | C12-C16 | 20 |
| BASF | Glucopon 625 UP | C12-C16 | 30 |
| BASF | Glucopon 50G | C12-C16 | 20 |
| Dow | Triton BG-10 | C8-C10 | 1591 |
| Dow | Triton CG-50 | C8-C10 | 871 |
| Dow | Triton CG-110 | C8-C10 | 1748 |
| Akzonobel | AG 6202 | C8 | 14000 |
| AkzoNobel | AG 6206 | C6 | 25000 |
| Wheatoleo | Appyclean 6781 | C8-C10 | <500 |
| Wheatoleo | Appyclean 6552 | C5&C10-C12 | 60-70 |
| Croda | Natrasense AG-810 | C8-C10 | 280 |
| Seppic | SIMULSOL SL 8 | C8 & C10 | 1530 |
| Seppic | SIMULSOL SL 826 | C8 & C16 | 131.5 |
| Seppic | SIMULSOL SL10 | C10 | 625 |
| Seppic | SMULSOL SL11 W | C11 | 1350 |
| Seppic | SIMULSOL SL 7G | C7 | 5138 |
| Seppic | SIMULSOL SL 26 | C10 & C16 | 80 |

In a preferred embodiment the alkyl polyglycoside is in an amount between about 7800 ppm and 130 ppm; preferably form about 6500 to about 780 ppm, and most preferably from about 4420 to about 1300 ppm in the use solution. On a weight percent basis the alkyl polyglycoside is from about 80.0 wt. % to about 1.3 wt. %; preferably from about 66.7 wt. % to about 8 wt. % and more preferably from about 45.3 wt. % to about 13.3 wt. % in the concentrate.

Amine Oxide Co-Surfactant

Semi-polar nonionic surfactants include the amine oxides, phosphine oxides, sulfoxides and their alkoxylated derivatives. Most preferred are amine oxide surfactants of a $R^1$ chain length of 8.

Amine oxides are tertiary amine oxides corresponding to the general formula:

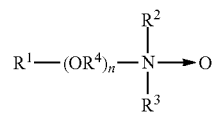

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an amidopropyl, alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

The amine oxide co-surfactant is preferably a C12 amine oxide surfactant. More preferably the amine oxide surfactant is a diethyl or dimethyl amine oxide surfactant. It is preferred that the amine oxide cosurfactant have a CMC greater than the quaternary ammonium compound.

The amine oxide co surfactant comprises from about 4050 ppm to about 67.5 ppm, preferably from about 3375 ppm to about 405 ppm and more preferably from about 2295 ppm to about 675 ppm in the use solution. On a weight percent basis the amine oxide comprises from about 90 wt. % to about 1.5 wt. %; preferably from about 75 wt. % to about 9.0 wt. % and more preferably from about 51.0 wt. % to about 15.0 wt. % in the concentrate.

Sequestering Agent/Chelant

The disinfectant cleaning composition may in addition comprise at least one sequestering agent/chelant. In general, a chelating agent is a molecule capable of coordinating (i.e., binding) the metal ions commonly found in water sources to prevent the metal ions from interfering with the action of the other ingredients. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelating agents include nitroloacetates and their derivatives, and mixtures thereof. In certain embodiments the composition is phosphate free.

Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA); N-hydroxyethyl-ethylenediaminetriacetic acid (HEDTA); tetrasodium ethylenediaminetetraacetic acid (EDTA); diethylenetriaminepentaacetic acid (DTPA); and alanine-N,N-diacetic acid; n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms. Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelating agents include polyaspartic acid or co-condensates of aspartic acid with other amino acids, $C_4$-$C_{25}$-mono-or-dicarboxylic acids and $C_4$-$C_{25}$-mono-or-diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

The chelant is present in the formulations of the invention from about 3000 ppm to about 10 ppm; preferably from about 2500 ppm to about 60 ppm and more preferably from about 1700 ppm to about 100 ppm in the use dilution. On a weight percent basis the chelant can comprise from about 30 wt. % to about 0.1 wt. % preferably from about 25 wt. % to about 0.4 wt. % and more preferably from about 17 wt. % to about 0.7 wt. % in the concentrate.

Optional Amine

The disinfectant cleaning composition of the invention may optionally comprise an amine, which is preferably an antimicrobial amine or acts synergistically with the active to increase specific antimicrobial performance. The amine may be a primary, secondary, or tertiary amine. Exemplary antimicrobial amines are listed below:

Aliphatic amine salts such as: ether ammonium salts.

Diamines such as: N-coco-1,3-propylene diamine (such as Duomeen®—Akzo Chemie America, Armak Chemicals), N-oleyl-1,3-propylene diamine (such as Duomeen®—Akzo Chemie America, Armak Chemicals), N-tallow-1,3-propylene diamine (such as Duomeen®—Akzo Chemie America, Armak Chemicals)

Diamine salts such as: diamine acetate (or other counterion), or diamine sales with the formulas $[(R_1)NH(R_2)NH_3]^+(CH_3COO)^-$ or $[R_1)NH_2(R_2)NH_3^{++}](CH_3COO)_2^-$ where $R_1$=a $C_{10}$-$C_{18}$ aliphatic group or an ether group having the formula $R_{10}OR_{11}$ where $R_{10}$=a $C_{10}$-$C_{18}$ aliphatic group and $R_{11}$=a $C_1$-$C_5$ alkyl group; and $R_2$=a $C_1$-$C_5$ alkylene group, or $R_1$=a $C_{10}$-$C_{18}$ aliphatic group derived from a fatty acid, and $R_2$=propylene Preferably, the antimicrobial amine is a secondary or tertiary alkyl amine having the general formula:

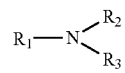

wherein $R_1$ is a $C_4$-$C_{20}$—, particularly $C_6$-$C_{18}$-alkyl, $C_5$-$C_{10}$—, particularly $C_6$-cycloalkyl, $C_7$-$C_{10}$, in particular $C_7$-arylalkyl or $C_6$-$C_{14}$—, particularly $C_6$-aryl group, $R_2$ an aminoalkyl group of formula —$(CH_2)$—$NH_2$, where n is a number from 2 to 10, preferably 2 to 6 and particularly preferably 2 to 3, and $R_3$ is hydrogen or $R_2$ is.

Preferably, $R_1$ is a $C_6$-$C_{18}$-alkyl group, preferably a $C_{10}$-$C_{18}$- and particularly preferably a dodecyl. $R_2$ is preferably an aminopropyl group and $R_3$ is hydrogen or $R_2$. When $R_2$ and $R_3$ are the same, the tertiary amine is preferably N-(3-aminopropyl)-N-dodecyl-1,3-propanediamine and N,N-bis (3-aminopropyl) laurylamine.

The tertiary amine, which is preferably a bis(3-aminopropyl)alkyamine, is known to be effective against bacteria, yeasts and molds in low concentrations. The bis(3-aminopropyl) alkylamine, wherein said alkyl has from about 6 to about 18 carbon atoms, is not known to have antiviral efficacy against Norovirus, Adenovirus and/or Polyomavirus. Preferably the bis(3-aminopropyl) alkylamine comprises N-(3-aminopropyl)-N-dodecylpropane-1,3-diamene. An exemplary N-(3-aminopropyl)-N-dodecylpropane-1,3-diamene is commercially available from Lonza (Basel, Switzerland) under the name Lonzabac.

The bis(3-aminopropyl) alkylamine, wherein said alkyl has from about 6 to about 18 carbon atoms, may be selected from the group comprising a bis(3-aminopropyl) $C_6$-$C_{18}$-alkylamine, a bis(3-aminopropyl) octylamine, a bis(3-aminopropyl) decyl amine, a bis(3-aminopropyl) dodecylamine, a bis(3-aminopropyl) quatrodecylamine, a bis(3-aminopropyl) hexadecylamine, a bis(3-aminopropyl) octadecylamine, or any combination thereof, and most preferred is a bis(3-aminopropyl) dodecylamine.

Additional amines include monoethanol amine, 2-amino-2-mthyl-1-propanol, diglycoamine and triethanol amine.

A disinfectant cleaning composition of the invention, preferably in form of a concentrate, may comprise about 1 wt.-% to about 30 wt.-%, preferably about 2 wt.-% to about 24 wt.-%, more preferred about 3 wt.-% to about 18 wt.-%, and most preferred of about 4 wt.-% to about 12 wt.-% of at additional antimicrobial such as an antimicrobial amine, preferably a tertiary alkyl amine, and more preferably a bis(3-aminopropyl) $C_8$-$C_{18}$ alkylamine; based on the total weight amount of the disinfectant cleaning composition of the invention, preferably in form of a concentrate.

A diluted disinfectant cleaning composition of the invention may comprise about 0.0005 wt.-% to about 6 wt.-%, preferably about 0.001 wt.-% to about 4 wt.-%, more preferred about 0.005 wt.-% to about 2 wt.-%, and most preferred of about 0.01 wt.-% to about 0.5 wt.-% at least one antimicrobial amine, preferably a tertiary alkyl amine, and more preferably a bis(3-aminopropyl) $C_8$-$C_{18}$ alkylamine; based on the total weight amount of the diluted disinfectant cleaning composition of the invention.

Additional Functional Ingredients

The compositions of the invention may be suitable for use in a variety of cleaning compositions, including applications of use set forth in the methods of the invention. In an aspect of the invention, the compositions may be further formulated to include additional surfactants and/or additional functional ingredients (e.g. surfactants, additional sanitizing agents, amines (e.g. alkanolamines), solvents, sequestrants, antiredeposition agents, glide agents and lubricants, thickening agents, bleaching agents, fillers, defoaming agents, dispersants, dyes, fragrances, preservatives, other adjuvants, hydrotropes, water and the like), such as those described, for example, in U.S. Pat. No. 7,341,983, which is herein incorporated by reference. It should be understood by those of skill in the art and others that the particular materials are given by way of example only, and that a broad variety of other functional materials may be used. For example, many of the functional materials relate to materials used in cleaning applications, but it should be understood that other embodiments may include functional materials for use in other applications.

In an aspect, the compositions include from about 0 wt-%-30 wt-% additional functional ingredients, from about 0 wt-%-20 wt-% additional functional ingredients, from about 0 wt-%-10 wt-% additional functional ingredients, or more preferably from about 0 wt-%-5 wt-% additional functional ingredients. In addition, without being limited according to the invention, all ranges recited are inclusive of the numbers defining the range and include each integer within the defined range.

Corrosion Inhibitor

According to the present invention, at least one corrosion inhibitor maybe used to prevent the corrosion of an article to be cleaned.

Preferably a silicate(s) corrosion inhibitor and more preferred a disilicate corrosion inhibitor can be used in the disinfectant cleaning composition according to the present invention. The silicate(s) and/or disilicate corrosion inhibitor can be an alkali silicate and/or alkali disilicate.

Other inhibitors that can be used can be selected from the group comprising calcium acetate, calcium chloride, calcium gluconate, calcium phosphate, calcium borate, calcium carbonate, calcium citrate, calcium lactate, calcium sulfate, calcium tartrate, benzotriazole, 1,2,3-benzotriazole and mixtures thereof.

More preferred, the corrosion inhibitor is a heterocyclic compound, a triazole derivate, such as a benzotriazole or 1,2,3-benzotriazole and mixtures thereof.

However, other corrosion inhibitors can be suitable added to the disinfectant composition of this invention include magnesium and/or zinc ions and Ca(NO2)2. Preferably, the metal ions are provided in water-soluble form.

Examples of useful water-soluble forms of magnesium and zinc ions are the water-soluble salts thereof including the chlorides, nitrates and sulfates of the respective metals. If any of the alkalinity providing agents are the alkali metal carbonates, bicarbonates or mixtures of such agents, magnesium oxide can be used to provide the Mg ion. The magnesium oxide is water soluble and is a preferred source of Mg ions. In order to maintain the dispersibility of the magnesium and/or zinc corrosion inhibitors in aqueous solution, and in the presence of agents which would otherwise cause precipitation of the zinc or magnesium ions, e.g., carbonates, etc. it might be advantageous to include a carboxylated polymer to the solution.

The useful carboxylated polymer corrosion inhibitors may be generically categorized as water-soluble carboxylic acid polymers such as polyacrylic and polymethacrylic acids or vinyl addition polymers, in addition to the acid-substituted polymers used in the present invention.

Of the vinyl addition polymer corrosion inhibitors contemplated, maleic anhydride copolymers as with vinyl acetate, styrene, ethylene, isobutylene, acrylic acid and vinyl ethers are examples.

The polymers tend to be water-soluble or at least colloidally dispersible in water. The molecular weight of these polymers may vary over a broad range although it is preferred to use polymers having average molecular weights ranging between about 1,000 up to about 1,000,000. These polymers have a molecular weight of about 100,000 or less and between about 1,000 and about 10,000.

The polymers or copolymers (either the acid-substituted polymers or other added polymers) may be prepared by either addition or hydrolytic techniques. Thus, maleic anhydride copolymers are prepared by the addition polymerization of maleic anhydride and another comonomer such as styrene.

The low molecular weight acrylic acid polymer corrosion inhibitors may be prepared by addition polymerization of acrylic acid or its salts either with itself or other vinyl comonomers.

Alternatively, such polymers may be prepared by the alkaline hydrolysis of low molecular weight acrylonitrile homopolymers or copolymers.

The polymers may be nonionic, anionic, cationic or amphoteric.

According to a more preferred embodiment of the present invention the disinfectant cleaning composition may comprises of at least one corrosion inhibitor selected from the group comprising silicate, sodium silicate, sodium disilicate, calcium acetate, calcium chloride, calcium gluconate, calcium phosphate, calcium borate, calcium carbonate, calcium citrate, calcium lactate, calcium sulfate, calcium tartrate, benzotriazole, 1,2,3-benzotriazole, or any combination thereof, more preferred at least one benzotriazole, and most preferred at least one 1,2,3-benzotriazole.

According to the invention, the disinfectant composition, preferably in form of a concentrate, may comprise about 0 wt.-% to about 4 wt.-%, preferably about 0.001 wt.-% to about 2 wt.-%, more preferred about 0.01 wt.-% to about 1 wt.-%, and most preferred of about 0.1 wt.-% to about 0.5 wt.-% of at least one corrosion inhibitor, preferably benzotriazole, and most preferred at least one corrosion inhibitor, preferably benzotriazole, and most preferred 1,2,3-benzotriazole; based on the total weight amount of the disinfectant cleaning composition of the invention, preferably in form of a concentrate.

A diluted disinfectant cleaning composition of the invention may comprise about 0 wt.-% to about 1 wt.-%, preferably about 0.00001 wt.-% to about 0.5 wt.-%, more preferred about 0.00005 wt.-% to about 0.5 wt.-%, and most preferred of about 0.0001 wt.-% to about 0.5 wt.-% of at least one corrosion inhibitor, preferably benzotriazole, and most preferred 1,2,3-benzotriazole; based on the total weight amount of the diluted disinfectant cleaning composition of the invention.

It should be understood that the disinfectant cleaning composition of the invention can be preferably free of a corrosion inhibitor.

Surfactants

In some embodiments, the compositions of the present invention include additional surfactant. Additional surfactants can include, for example anionic surfactants, and zwitterionic surfactants may be used. In some embodiments, the compositions of the present invention include about 0.4 wt % to about 12.8 wt % of a surfactant. In some embodiments, the compositions of the present invention include about 62.5 ppm to about 2000 ppm of a surfactant.

In some embodiments the composition will be free of all surfactants other than the quaternary ammonium chloride, amine oxide and alkyl polyglycoside.

In some embodiments, the composition will be free of all cosurfactants that have a CMC lower than that of the quaternary ammonium chloride.

Semi-Polar Nonionic Surfactants

The semi-polar type of nonionic surface active agents are the preferred class of surfactants useful in compositions of the present invention.

The compositions of the invention may optionally include surfactants such as the following.

Nonionic Surfactants

Suitable additional nonionic surfactants for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like. In other cases, extended surfactants may be included. Extended surfactants are those surfactants that contain a moderately hydrophobic linker group, typically a higher alkylene oxide such as propylene oxide, between the hydrophobic alkyl tail and the hydrophilic head. The head group is typically polypropylene glycol, but can be carboxylate, sulfate or sulfonate. An example is the Lutensol XL series from BASF.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylethoxy carboxylates of the following formula:

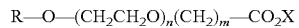

R—O—$(CH_2CH_2O)_n(CH_2)_m$—$CO_2X$ in which R is a $C_8$ to $C_{22}$ alkyl group or in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_5$-$C_{16}$ alkyl group. In some embodiments, R is a $C_{12}$-$C_{14}$ alkyl group, n is 4, and m is 1.

In other embodiments, R is

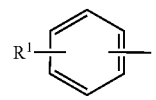

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid. Phosphate ester type surfactants may also be included, for example, Rhodafac RA-600 from Solvay.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Commercially prominent imidazoline-derived amphoterics that can be employed in the present compositions include for example: Cocoamphopropionate, Cocoamphocarboxypropionate, Cocoamphoglycinate, Cocoamphocarboxyglycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na$)$_2$—$CH_2$—$CH_2$—OH or $C_{12}$-alkyl-C(O)—N(H)—$CH_2$—$CH_2$—$N^+$($CH_2$—$CO_2Na$)$_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Solvay Inc., Cranbury, N.J.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

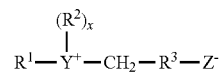

wherein $R_1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfoniol-3-hydroxypentane-1-sulfate; 3-[P,P-diethyl-P-3,6,9-trioxatetracosanephosphonio]-2-hydroxypropane-1-phosphate; 34N,N-dipropyl-N-3-dodecoxy-2-hydroxypropyl-ammonio]-propane-1-phosphonate; 3-(N,N-dimethyl-N-hexadecylammonio)- propane-1-sulfonate; 3-(N,N-dimethyl-N-hexadecylammonio)-2-hydroxy-propane-1-sulfonate; 4-[N,N-di(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

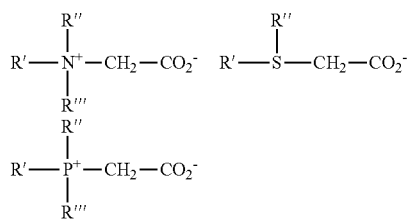

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Wetting or Defoaming Agents

Also useful in the compositions of the invention are wetting agents. Wetting agents function to increase the surface contact or penetration activity of the antimicrobial composition of the invention. Wetting agents which can be used in the composition of the invention include any of those constituents known within the art to lower the surface activity of the composition of the invention. Typical superwetters are silicone copolyols and acetylenic diols. They serve to provide wetting, leveling and spreading of the composition on difficult-to-wet substrates.

Solvents

The compositions of the invention may comprise one or more organic solvents, but preferably are organic solvent free. Suitable solvents include, but are not limited to, alcohols, ethanol, isopropanol, 2-butoxy ethanol, 1-decanol, benzyl alcohol, glycerin, glycols, ethylene glycol, diethylene glycol, butoxy diglycol, triethylene glycol, tetraethylene glycol, propylene glycol, dipropylene glycol, hexylene glycol, glycol ethers, esters, or combinations thereof. Suitable alcohols include, but are not limited to, ethanol, isopropanol, 2-butoxy ethanol, 1-decanol, glycerin, or any combination thereof. Alkylene glycols having from about 2 to 6 carbon atoms, straight or branched chain lower alkyl alcohols, glycerol, propylene carbonate, alkylene glycol mono alkyl ethers where the alkylene portion has from about 2 to 6 carbon atoms and the alkyl portion has about 1 to 6 carbon atoms, poly alkylene glycol mono alkyl ethers where each alkylene portion has from about 2 to 6 carbon atoms and the alkyl portion has about 1 to 6 carbon atoms, alkyl acetates where the alkyl portion has from about 1 to 6 carbon atoms, pine oil, terpenes and mixtures thereof. Examples of such solvents are the following:

Dodecane, Propylene Carbonate, Diethylene glycol mono-n-butyl ether, Isopropyl Alcohol, Butyl acetate, Glycerol, Pine Oil Hexylene Glycol, Orange oil, d-limonene or other fragrance ingredients may be present at low levels. Glycol ether solvents are commonly used in aqueous cleaning and disinfecting formulas. Glycol ethers can be formed from ethylene or propylene oxide yielding E and P series glycol ethers respectively. Examples are diethylene glycol butyl ether and tripropylene glycol butyl ether.

According to the invention, the disinfectant composition, preferably in form of a concentrate, may comprises from about 0.2%, to about 20%, preferably from about 1% to about 15%, more preferably from about 2% to about 10%.

Alkaline Source

The composition can include a source of alkalinity can be any source of alkalinity that is compatible with the other components of the disinfectant cleaning composition and that will provide the solution with the desired pH.

Exemplary sources of alkalinity include alkali metal hydroxides, alkali metal salts, amines, ammonium hydroxide, and mixtures thereof.

Exemplary alkali metal hydroxides include sodium hydroxide, potassium hydroxide, and lithium hydroxide. Exemplary alkali metal salts include sodium carbonate, trisodium phosphate, potassium carbonate, and mixtures thereof.

Exemplary amines include alkanolamine selected from the group comprising triethanolamine, monoethanolamine, diglycolamine and mixtures thereof.

The source of alkalinity, preferably an alkali metal hydroxide, may be added to the disinfectant cleaning composition in a variety of forms, including for example in the form of solid beads, dissolved in an aqueous solution or a combination thereof. Alkali metal hydroxides are commercially available as pellets or beads having a mix of particle sizes ranging from 12-100 U.S. mesh, or as an aqueous solution, as for example, as about 45 wt. %, about 50 wt. % and about 73 wt. % solution. Preferably the alkalinity source is selected from the group comprising alkali metal hydroxides, alkali metal salts, phosphates and/or amines and mixtures thereof, preferably triethanol amine, sodium hydroxide, potassium hydroxide, sodium carbonate, and/or sodium bicarbonate and mixtures thereof and more preferred ethanolamine.

According to the invention, the disinfectant composition, preferably in form of a concentrate, may comprises about 0 wt.-% to about 10 wt.-%, preferably about 0.1 wt.-% to about 8 wt.-%, more preferred about 0.5 wt.-% to about 5 wt.-%, and most preferred of about 1 wt.-% to about 3 wt.-% of at least one alkali source, and more preferred ethanolamine; based on the total weight amount of the disinfectant cleaning composition of the invention, preferably in form of a concentrate.

A diluted disinfectant cleaning composition of the invention may comprise about 0 wt.-% to about 0.5 wt.-%, preferably about 0.00025 wt.-% to about 0.4 wt.-%, more preferred about 0.001 wt.-% to about 0.2 wt.-%, and most preferred of about 0.004 wt.-% to about 0.1 wt.-% of at least one alkali source, and more preferred ethanolamine; based on the total weight amount of the diluted disinfectant cleaning composition of the invention.

It should be understood that the disinfectant cleaning composition of the invention can be preferably free of an alkali source.

It should be understood that the disinfectant cleaning composition of the invention can be preferably free of phosphates.

Acid Source

An acid may be provided to adjust the pH of the solution. Organic acids such as lactic, citric, hydroxyacetic, succinic may be used. Alternately inorganic acids such as sulfuric, sulfamic and hydrochloric may be used. Depending on the acid it may also contribute other benefits to the formula, such as divalent metal sequestration.

Defoaming Agents

Also useful in the compositions of the invention are defoaming agents.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfonated or sulfated derivatives; fatty acids and/or their soaps such as alkali, alkaline earth metal soaps; and phosphates and phosphate esters such as alkyl and alkaline diphosphates, and tributyl phosphates among others; and mixtures thereof.

In some embodiments, the compositions of the present invention can include antifoaming agents or defoamers which are of food grade quality given the application of the method of the invention. To this end, one of the more effective antifoaming agents includes silicones. Silicones such as silicone co-polyols, dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others.

Thickening or Gelling Agents

The compositions of the present invention can include any of a variety of known thickeners. Suitable thickeners include cellulosic thickeners, preferably nonionic, such as hydroxyethyl cellulose and hydroxypropyl cellulose. Natural gums such as xanthan gum, Cationic guar, guar gum, or other gums from plant mucilage; polysaccharide based thickeners, such as alginates, starches are also acceptable in certain cases, and other cellulosic polymers (e.g., carboxymethyl cellulose); polyacrylates thickeners; and hydrocolloid thickeners, such as pectin. HEUR polymers such as Acusol 880 from The Dow Chemical Corp. Midland Mich. may also be included. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition.

Concentrate

The disinfectant cleaning composition can be presented in a liquid concentrated form. The source of alkalinity and addition of the a polar carrier, (water) are provided so that the concentrated, preferably aqueous, liquid composition of the disinfectant cleaning composition according to the present invention may have a pH in the range of about 5 pH to about 14 pH, preferably is from about 6 pH to about 11 pH, and more preferred is from about 7 pH to about 10 pH.

According to one embodiment, the disinfectant cleaning composition of the invention, preferably in form of a concentrate, may comprise: about 1 wt.-% to about 30 wt.-%, preferably about 2 wt.-% to about 24 wt.-%, more preferred about 3 wt.-% to about 18 wt.-%, and most preferred of about 4 wt.-% to about 11 wt.-% of at least one biocidal quaternary ammonium compound, preferably a quaternary ammonium chloride of di-alkyl dimethyl ammonium chloride, further preferred a mixture of a N-alkyl($C_8$-$C_{10}$)dimethyl ammonium chloride including di$C_8$, $C_8$, $C_{10}$ and di$C_{10}$ dimethyl ammonium chloride, and/or mixtures thereof; about 1 wt.-% to about 30 wt.-%, preferably about 2 wt.-% to about 24 wt.-%, more preferred about 3 wt.-% to about 18 wt.-%, and most preferred of about 4 wt.-% to about 12 of at least one antimicrobial amine, preferably a bis(3-aminopropyl) $C_8$-$C_{18}$ alkylamine, and most preferred N-(3-aminopropyl)-N-dodecylpropane-1,3-diamene; about 0.001 wt.-% to about 10 wt.-%, preferably about 0.005 wt.-% to about 8 wt.-%, more preferred about 0.01 wt.-% to about 5 wt.-%, and most preferred of about 0.05 wt.-% to about 2 wt.-% chelating agent. The concentrate can be supplied as a solid block, or powder produced by extrusion, casting, pressing, or other means and will be substantially free of water in those cases.

Ready-to-Use Composition

The disinfectant cleaning composition of the invention can be present in form of a diluted or so called "ready-to-use" composition. The source of alkalinity and addition of the solvent, preferably water, are provided so that the diluted, preferably aqueous, liquid composition of the disinfectant cleaning composition according to the present invention may have a pH in the range of about 6 pH to about 12 pH, preferably is from about 7.5 pH to about 11.5 pH, and more preferred is from about 7 pH to about 11.0 pH.

According to one aspect of the invention, the concentrated disinfectant cleaning composition can be diluted with a at least one carrier preferably water, by a factor of 5 to 1000, preferably 10 to 500 and further preferred 20 to 400 to obtain the diluted disinfectant cleaning composition of the invention.

According to one aspect, the diluted disinfectant cleaning composition (ready-to-use) can be diluted with a carrier (water), to a 0.25% to 4.0% solution from a concentrated disinfectant composition. The water may be hard water, wherein hard water comprises dissolved minerals including calcium, magnesium, and manganese.

It will be appreciated that the actual concentration of components in a composition of the invention will depend on the intended use of that composition. For disinfecting uses, such as cleaning of hospital wards and equipment to help prevent the spread of disease such as those caused by *Staphylococcus aureus*, Norovirus, Adenovirus and Polyomavirus, higher concentrations are required than for certain sanitizing applications.

Use of the Disinfectant Composition

According to an embodiment of the invention, a method of employing a sanitizing composition comprises:

contacting a surface, article, and/or substrate with a sanitizing composition comprising:

a quaternary ammonium biocide, an amine oxide co-surfactant, an alkyl polyglycoside co-surfactants, and a chelant, wherein the compositions is essentially free of solvents. According to another aspect of the invention, the contacting results in inactivation and/or reduction of infectious agents on the surface, article, and/or substrate. The infectious agents may comprise bacteria, viruses, and/or yeasts. Preferably, the infectious agents are vegetative bacteria and Norovirus.

The disinfectant cleaning composition according to the invention can be used for inactivating and/or reducing infectious agents, comprising bacteria, virus, and/or yeasts.

The disinfectant cleaning composition of the invention gives a reduction in the number of microorganisms and viruses, preferably vegetative bacteria including *Staphylococcus aureus, Salmonella typhi* and *Pseudomonas aeruginosa*, and viruses including Norovirus. The antimicrobial efficacy is preferably (non-food contact surface) sanitizing, which is at least log 3.0. More preferably the efficacy is disinfectant level passing the EPA GST and/or UDT test method, or whatever method the Agency species. Most preferably a disinfectant cleaning composition of the invention having a residual sanitizing effect and tested in this manner will give a log reduction of at least about 3.0.

In use the compositions of the invention act to substantially inactivating and/or reducing infectious agents, comprising bacteria, virus, and/or yeasts, for example on surfaces in hospitals, hotels, schools, colleges, industrial and commercial facilities and retail stores. Using the disinfectant compositions according to the invention can take the form of a concentrate that can be diluted and combined to provide a ready-to-use solution, and as a ready-to-use liquid composition that can be used to clean articles having a metal or plastic surface, such as tabletops, doorknobs, painted surfaces, television remote controls, computer keyboards and other high touch objects that may participate in germ transmission.

Metal surfaces and/or plastic surfaces in need of disinfecting and cleaning are found in several locations. Exemplary locations include machine parts, vehicles, work surfaces, tabletops, appliance handles, lavatory surfaces, hotel room surfaces.

Metal surfaces that can be disinfected include iron-based metals such as iron, iron alloys, e.g. steel, tin, aluminum, copper, tungsten, titanium, molybdenum, etc., for example. The structure of the metal surface to be disinfected can vary widely. Thus, the metal surface and/or plastic surface can be as a metal and/or plastic part of complex configuration, sheeting, coils, rolls, bars, rods, plates, disks, etc.

More preferred is the use of the disinfectant cleaning composition of the invention, in particular the ready-to-use composition to disinfect coated wood, plastic, metal, glass windows and mirrors, bathtubs, shower surfaces, porcelain fixtures and the like.

The disinfectant composition, preferably the ready-to-use-composition, can be applied to a surface by wiping the treated surface with a saturated cloth, mop, sponge or other suitable delivery mechanism. The composition can also be applied by spraying and/or flooding the surface with the disinfectant composition or by immersion of items in the use solution. The liquid is normally allowed to keep the surface wet for the specified contact time to ensure the desired level of antimicrobial effect.

The disinfectant cleaning composition of the invention is maybe suitable for a variety of consumer applications. Examples of the formulations of the invention include, but are not limited to surface cleanings such as those intended for use in bathrooms, kitchens, living areas hard floor cleanings carpet cleanings furniture cleanings, glass/mirror cleanings; toilet care products including solid toilet cleanings. The use solution of the composition may have a pH of 7 pH to about 14 pH, preferably is from about 7 pH to about 13 pH, and more preferred is from about 7 pH to about 12 pH; cleaning products intended for use outdoors such as those for cleaning for wood, stone, concrete or plastics, for example patio cleaning, garden furniture cleanings/treatments, BBQ cleanings, wall and fence cleanings/treatments, products for cleaning surfaces that have regular & high incidence of contact; products for cleaning and/or deodorizing vehicles such as cars.

Method of Making

The invention also provides a process for making the compositions of the invention. The process comprises the steps of mixing at least part of at least one biocidal quaternary ammonium compound, preferably a quaternary ammonium chloride of di-alkyl dimethyl ammonium chloride, wherein said alkyl has from about 8 to about 10 carbon atoms, further preferred a didecyl dimethyl benzyl ammonium chloride, Decyl octyl dimethyl ammonium chloride dioctyl dimethyl ammonium chloride mixture, and adding the at least one biocidal amine, preferably a bis(3-aminopropyl)alkylamine wherein said alkyl has from about 6 to about 18 carbon atoms, further preferred N-(3-aminopropyl)-N-dodecylpropane-1,3-diamine; wherein the weight-% ratio of a) a biocidal quaternary ammonium compound, to b) a biocidal tertiary amine, is in the range of about 0.1:1 to about 1:0.1, in the appropriate amounts to achieve the synergy of the two. An alkylpolyglucoside surfactant exhibiting a CMC of at least 1000, more preferably above 4000. An alkyl amine oxide surfactant wherein the alkyl group is C8-C18 and exhibiting a CMC above that of the quaternary ammonium chloride. A chelating agent. Preferably an aminocarboxylate chelating agent, and agitating the resulting mixture until a homogenous solution is formed. Typically, the process to produce the compositions of the invention is carried out at room temperature with stirring. The present invention provides compositions obtainable by the process set out above. The compositions of the invention may be prepared in a concentrated form and diluted with water when used to the diluted disinfectant cleaning solution. The concentrate may be diluted with hard water.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

Exemplary Compositions of the Invention

Examples of use solution formulations of the invention are as follows:

|  | Most preferred | More preferred | Preferred |
|---|---|---|---|
| Quaternary ammonium | 1700-500 ppm | 2500-300 Ppm | 3000-50 ppm |
| Alkyl poly glycoside | 4420-1300 ppm | 6500-780 Ppm | 7800-130 ppm |
| Amine oxide | 2295-675 ppm | 3375-405 Ppm | 4050-67.5 ppm |
| Chelant | 1700-100 ppm | 2500-60 Ppm | 3000-10 ppm |

Examples of the concentrate composition at a dilution of 2 oz.: 1 gallon are as follows:

|  | Most preferred | More preferred | Preferred |
|---|---|---|---|
| Quaternary ammonium | 22.7-6.7% | 33.3-4.0% | 40.0-0.7% |
| Alkyl poly glycoside | 45.3-13.3% | 66.7-8.0% | 80.0-1.3% |
| Amine oxide | 51.0-15.0% | 75.0-9.0% | 90.0-1.5% |
| Chelant | 17-0.7% | 25-0.4% | 30-0.1% |

Examples of useful ranges of the components for the concentrated disinfectant cleaning composition of the invention include those provided in the following table, with water making up any remainder:

| Component | Weight Percent (wt-%) | Preferred wt-% | More Preferred wt-% | Most preferred wt-% |
|---|---|---|---|---|
| biocidal quaternary ammonium compound | 1-30 | 2-24 | 3-18 | 4-11 |
| amine | 1-30 | 2-24 | 3-18 | 4-12 |
| Alkyl polyglycoside | 1-30 | 2-24 | 3-18 | 4-12 |
| Amine oxide | 1-30 | 2-24 | 3-18 | 4-12 |
| other functional ingredients | 0-30 | 0-20 | 0-10 | 0-5 |

Examples of useful ranges of the components for a use solution of the disinfectant cleaning composition of the invention include those provided in the following table, with water making up any remainder:

| Component | Weight Percent (wt-%) | Preferred wt-% | More Preferred wt-% | Most preferred wt-% |
|---|---|---|---|---|
| biocidal quaternary ammonium compound | 0.0001-3 | 0.0005-2 | 0.001-1 | 0.005-0.5 |
| amine | 0.0005-3 | 0.001-2 | 0.005-1 | 0.01-0.5 |
| Alkyl polyglycoside | 0-5 | 0.0001-3 | 0.001-2 | 0.01-1 |
| Amine oxide | 0-5 | 0.0001-3 | 0.001-2 | 0.01-1 |
| other functional ingredients | 0-10 | 0-5 | 0-1 | 0-0.1 |

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Many glass cleanings use linear alkyl polyglycosides (APGs), usually of chain lengths ranging from C8-C16, and propylene glycol due to its low volatility. The performance of various combinations of these was tested. Each experiment was given a visual performance of 'good', 'ok', or 'bad'. Performance was also tested quantitatively by analyzing the % streaky area where <2=good, 2<ok<7, and >7=bad.

Area Analysis Using Software

Open up Image J

1. File>Open>find your image
2. Split into red, green and blue channels. Image>Color>Split Channels. Three individual images from the original that are in black and white are generated. Image titles will show each channel. The red image is considered the best for analyzing.
3. Image>Adjust>Threshold. Adjust the second bar to change the colorful area which covers the area you want to calculate.
4. Select Rectangular tool in the tool bar to restrict the area you want to calculate. For instance, in the sample image, if no selection is made, ImageJ will calculate all the red area.
5. Analyze>Analyze Particles. Tick Display Results (shows every area) and Summarize (the sum area of the selected). "Exclude on the edges" will eliminate the holes on the edge and "Include Holes" will add up the hole inside the area. In the Summary box, Total Area and % area is the final result. The % area is the % streaky area.

The 'quat blend' is Bardac 2250/Barquat MB-50 at 325/325 ppm.

| Trade name | chemical name |
|---|---|
| Barquat MB-50 | Alkyldimethylbenzylammonium chloride |
| Bardac 2250 | Didecyldimethylammoniumchloride |
| AG 6202 | a-D-Glucopyranoside, 2-ethylhexyl |
| Barlox 12 | Cocoamine oxide |
| N/A | Trisodium citrate dihydrate |
| Glucopon 215 | alkyl polyglucosides based on natural fatty alcohol C8-C10, |

| Exp # | Quat blend | Glucopon 215 | Propylene glycol | Visual rating (good, ok, bad) | % streaky area | Pass Y/Close/N |
|---|---|---|---|---|---|---|
| Control | 750 | 0 | 0 | bad | 35.6 | N |
| A1 | 750 | 975 | 0 | bad | 8 | N |
| A2 | 750 | 975 | 1500 | ok | 2 | Close |
| A3 | 750 | 975 | 3000 | bad | 3 | N |
| A4 | 750 | 975 | 4500 | bad | 1 | N |
| A5 | 750 | 1950 | 0 | good | 1 | Y |
| A6 | 750 | 1950 | 1500 | good | 0 | Y |
| A7 | 750 | 1950 | 3000 | bad | 3 | N |
| A8 | 750 | 1950 | 4500 | bad | 1 | N |
| A9 | 750 | 2925 | 0 | good | 0 | Y |
| A10 | 750 | 2925 | 1500 | good | 1 | Y |

From the results one can see that the addition of propylene glycol reduced streaking (A1-A2) close to an acceptable level. Addition of Glucopon 215 reduced streaking to an acceptable level. Surprisingly, at high levels of propylene glycol, surface appearance worsens (A7-A8), and a 0 addition the streaky area was 0. Many of the experiments containing propylene glycol left small, slow-drying, clear droplets which are not acceptable.

Microbial Testing

Formulas with passable or ok glass performance and formulas of interest were then tested for antimicrobial efficacy. Log reduction results are considered significantly different if the numbers differ by more than 0.5. Therefore, formulas with greater than 3.3 log reduction are considered to significantly improve micro efficacy and formulas with less than 2.3 log reduction are considered to significantly reduce micro efficacy when compared to the quat control.

| Exp # | Quat blend | Glucopon 215 | Propylene glycol | OECD log reduction S. aureus | Better, worse, or same (compared to control) |
|---|---|---|---|---|---|
| Control | 750 | 0 | 0 | 2.8 | control |
| A1 | 750 | 975 | 0 | 2.6 | same |
| A2 | 750 | 975 | 1500 | 2.0 | worse |
| B1 | 750 | 0 | 1500 | 2.7 | same |
| B2 | 750 | 0 | 3000 | 2.1 | worse |

Although experiment A2 was almost at an acceptable level of streaking, quat antimicrobial activity is significantly reduced. Increasing propylene glycol levels also appears to inhibit antimicrobial activity. Although propylene glycol is a popular component in glass cleanings, it is not necessary and may be detrimental to quat antibacterial activity at certain levels.

Amine oxides are also commonly used surfactants and were tested with Glucopon 215.

| Exp # | Quat blend | Glucopon 215 | C8 Amine oxide | C12 Amine oxide | OECD log reduction S. aureus | Better, worse, or same (compared to control) |
|---|---|---|---|---|---|---|
| Control | 750 | 0 | 0 | 0 | 2.8 | control |
| A1 | 750 | 975 | 0 | 0 | 2.6 | same |
| C1 | 750 | 0 | 480 | 0 | 1.9 | worse |
| C2 | 750 | 0 | 0 | 510 | 2.3 | same |
| C3 | 750 | 195 | 600 | 0 | 2.7 | same |
| C4 | 750 | 195 | 0 | 450 | 3.6 | better |

Surprisingly, quat paired with a C12 amine oxide (Barlox 12) and an APG (Glucopon 215) showed improved antimicrobial kill. Quat paired with C8 amine oxide (FMB AO-8) and Glucopon 215 was not able to boost kill. The quat and C12 amine oxide combination was not able to boost kill, neither was the quat and Glucopon 215 combination. Quat, C12 amine oxide, and APG are needed together for this synergistic effect. To further investigate, streak free (% streaky area of zero) formulations of quat, APG, and amine oxide were tested using the OECD method with the addition of a chelant. Four log reduction is considered passing for this method. The best of these was tested using the GST method.

when present at very low amounts, whereas high CMC surfactants will not form micelles unless the surfactants are present at very high concentrations. But, at least some surfactants with extremely high or no CMCs, while they may be quat-compatible, are not effective at improving glass performance, possibly as they are very poor surfactants (C4 APGs, for example). Therefore, by choosing an APG with a CMC within a certain range we are able to achieve a fast, high kill without a high amount of active present, and simultaneously deliver good glass cleaning performance.

| Formula | Amount (ppm) | Water | Contact time | Soil | OECD Log reduction Staph | OECD Log reduction Pseudo | GST Staph | Pass (Y/N) |
|---|---|---|---|---|---|---|---|---|
| Quat blend/Barlox 12/Glucopon 215/Acid EDTA | 750/900/1300/200 | DI | 5 min | Yes | 2.8 | 4.1 | | N |
| Quat blend/Barlox 10/Glucopon 215/Acid EDTA | 750/1200/1950/200 | DI | 5 min | Yes | 2.1 | 5.3 | | N |
| Quat blend/Barlox 12/AG 6206/Acid EDTA | 750/1350/2625/200 | DI | 5 min | Yes | 4.0 | 4.6 | | Y |
| Quat blend/Barlox 12/AG 6202/Acid EDTA | 750/1350/2600/200 | DI | 5 min | Yes | 4.6 | 5.3 | 59/60 | Y |
| Quat blend/Barlox 12/Glucopon 225 DK/Acid EDTA | 750/900/1400/200 | DI | 5 min | Yes | 3.5 | 3.5 | | N |
| Quat blend/Barlox 10/Glucopon 225 DK/Acid EDTA | 750/1200/1400/200 | DI | 5 min | Yes | 2.5 | 5.3 | | N |

Surprisingly, the two formulas that passed the OECD method contained Barlox 12 and a high CMC APG (see table below) and showed significantly higher log reduction, especially against *S. aureus*.

As the formula above delivered a 59/60 on a GST test in DI water, the quat concentration was increased for testing in 400 ppm hard water using the GST and Residual Self-Sanitizer (RSS) method.

| Formula | Amount (ppm) | Water | Contact time | Soil | GST Staph | GST Pseudo | RSS Staph Enterobac |
|---|---|---|---|---|---|---|---|
| Quat blend/Barlox 12/AG 6202/EDTA | 1000/1350/2600/200 | 400 ppm | 5 min | Yes | 60/60 | | 99.98 |

| Surfactant | Type | CMC (mg/L) | CAS # |
|---|---|---|---|
| Glucopon 215 | C8-C10 linear APG | 200 | 68515-73-1 |
| Glucopon 225 DK | C8-C10 linear APG | 250 | 68515-73-1 |
| Triton CG-50 | C8-C10 linear APG | 871 | 68515-73-1 |
| Triton CG-110 | C8-C10 linear APG | 1,748 | 68515-73-1 |
| Triton BG-10 | C8-C10 linear APG | 1,591 | 68515-73-1 |
| AG 6201 | C8 linear APG | 4,000 | |
| AG 6210 | C8-C10 branched APG | ~500 | |
| AG 6202 | C8 branched APG | 14,000 | 125590-73-0 |
| AG 6206 | C6 linear APG | 25,000 | |

A theory regarding why using high CMC surfactants yielded better antibacterial results was developed: Surfactants in formulas with quaternary ammonium compounds (quats) form mixed micelles with the quats, effectively reducing the amount of free quat in solution, which results in lower kill. Low CMC surfactants form micelles even As this formula exhibits superior wetting qualities and high kill due to the special surfactant combination, the chemistry is able to pass a glass performance, 5 minute GST, Norovirus efficacy and residual self-sanitizer test, which are claims no other commercially available chemistry can make.

Example 2

Different types of quaternary ammonium compounds exhibit different antimicrobial efficacy, hard water tolerance, and solubility. For this reason, various quats were tested for efficacy.

| Formula | Amount (ppm) | Water | OECD log reduction Staph |
|---|---|---|---|
| Bardac MB-50/Bardac 2250 | 325/325 | DI | 2.8 |
| Bardac 2250 | 750 | 400 ppm | 1.6 |
| Bardac 22c50 (Carboquat) | 750 | 400 ppm | 1.8 |

| Formula | Amount (ppm) | Water | OECD log reduction Staph |
| --- | --- | --- | --- |
| Bardac 2050 | 750 | 400 ppm | 3.4 |
| Bardac MB-50 | 750 | 400 ppm | NDR |

Bardac 2050 (mixed dialkyl) exhibited significantly higher log reduction against staph when compared to Bardac 2250 (didecyl), Bardac 22c50 (didecyl, carbonate counter ion), Bardac MB-50 (alkyldimethyl benzyl ammonium chloride, ADBAC), and a Bardac 2250/Bardac MB-50 blend.

Additional testing was done to determine if this effect was reproducible in a full formula against a gram negative organism at varying water hardness (NDR is a log reduction of less than 3):

| Formula | Amount (ppm) | Water | OECD log reduction Pseudo |
| --- | --- | --- | --- |
| Quat blend/Barlox 12/AG 6202/NaCitrate | 1000/1350/2600/200 | DI | 3.9 |
| Bardac 2050/Barlox 12/AG 6202/NaCitrate | 1000/1350/2600/200 | DI | 5.9 |
| Quat blend/Barlox 12/AG 6202/NaCitrate | 1000/1350/2600/200 | 250 ppm | NDR |
| Bardac 2050/Barlox 12/AG 6202/NaCitrate | 1000/1350/2600/200 | 250 ppm | 3.5 |
| Quat blend/Barlox 12/AG 6202/NaCitrate | 1000/1350/2600/200 | 400 ppm | NDR |
| Bardac 2050/Barlox 12/AG 6202/NaCitrate | 1000/1350/2600/200 | 400 ppm | 3.0 |

The formula with the mixed dialkyl quats (no ADBAC) performed significantly better in DI, 250 ppm, and 400 ppm hard water against the gram negative organism. Variations of this formula were then tested against feline calicivirus, which is norovirus surrogate. Bardac 2050 by itself was the control.

A norovirus claim is very important for hard surface disinfectants, but can be difficult to achieve. Norovirus is an unenveloped virus, which is generally more difficult to inactivate than enveloped viruses.

| Formula | Amount | pH | FCV log reduction | Pass/Fail |
| --- | --- | --- | --- | --- |
| Bardac 2050 | 1000 | ~7.5 | 5.75 | Pass |
| Bardac 2050/Barlox 12/AG 6202/NaCitrate | 1000/1350/2600/200 | ~7.5 | 1.5 | Fail |
| Bardac 2050/Barlox 12/AG 6202/NaCitrate | 1000/1350/2600/200 | ~11 | 2.5 | Fail |
| Bardac 2050/Barlox 12/AG 6202/NaCitrate | 1200/1350/2600/200 | ~11 | 2.25 | Fail |

Increasing quat concentration and formula pH increased log reduction, but log reduction was not high enough to pass. Bardac 2050 by itself was able to pass, but none of the full formulas passed. This implies that one of the surfactants (or both) is interfering with kill. Quat was tested with each surfactant alone to determine which surfactant was interfering. Also, Lonzabac 12 was added to one formula. Streak testing was performed on each formula. FCV (feline calicivirus) testing was done in 400 ppm hard water with a 10 minute contact time and soil.

| Formula | Amount | pH | Visual steak rating | FCV log reduction | Pass/Fail |
| --- | --- | --- | --- | --- | --- |
| Bardac 2050/Barlox 12 | 1000/1350 | ~7.5 | Ok | 2.5 | Fail |
| Bardac 2050/AG 6202 | 1000/2600 | ~7.5 | Bad | 5.25 | Pass |
| Bardac 2050/Barlox 12/AG 6202/EDTA/Lonzabac 12 | 1000/1350/2600/200/810 | 11 | Good | 4.75 | Pass |

Barlox 12 interferes with FCV kill, while AG 6202 does not. However, Barlox 12, however, demonstrates a reduces streaking effect. The formula with the addition of Lonzabac 12 passes the FCV test and does not streak. The Quat/Amine oxide/APG/Chelant formula alone is not effective against FCV, and the addition of Lonzabac 12 is necessary for the norovirus claim.

AG 6202 is a low foaming alkyl glucoside, non-ionic surfactant, based on a short chain fatty alcohol and glucose.

Barlox 12 is a cocoamine oxide surfactant

Lonzabac 12 is a Bis(3-aminopropyl) dodecylamine

Bardac 2050 Blend of C8, C10 dialkyl dimethyl ammonium chlorides

Bardac 2250 (didecyl ammonium chlorides),

Bardac 22c50 (didecyl, quat, carbonate counter ion),

Bardac MB-50 Alkyl Dimethyl Benzyl Ammonium Chloride (ADBAC)

Bardac 2250/Bardac MB-50 blend.

What is claimed is:

1. A sanitizing composition comprising:
   from about 0.7 wt. % to about 40.0 wt. % of a a dialkyl quaternary ammonium compound free of benzyl or aromatic quaternary substituents;
   from about 8 wt. % to about 80.0 wt. % of an alkyl polyglycoside surfactant;
   from about 9 wt. % to about 90.0 wt. % of a C12 or higher amine oxide surfactant; and
   from about 0.1 wt. % to about 4.0 wt. % of a chelant;
   wherein the composition does not contain organic solvent and wherein the alkyl polyglycoside surfactant having a critical micelle concentration (CMC) of 1000 or more does not interfere with the biocidal activity of the quaternary ammonium compound.

2. The composition of claim 1, further comprising a primary, secondary, or tertiary amine.

3. The composition of claim 1 further comprising bis(3-aminopropyl) alkylamine.

4. The composition of claim 1 wherein the composition is diluted with water by a factor of 10 to 1000.

5. The composition of claim 4, wherein the composition is diluted by a factor of 50 to 500.

6. A method of residual sanitizing a surface comprising:
   Contacting a surface, article, and/or substrate with the sanitizing composition of claim 1.

7. The method of claim 6, wherein the contacting results in inactivation and/or reduction of infectious agents on the surface, article, and/or substrate.

8. The method of claim 6, wherein the infectious agents comprise one or more of bacteria, viruses and/or yeasts.

9. A residual sanitizing composition comprising:
   from about 3000 ppm to about 50 ppm of a dialkyl quaternary ammonium compound free of benzyl or aromatic quaternary substituents;
   from about 7800 ppm to about 130 ppm of an alkyl polyglycoside surfactant;
   from about 4050 ppm to about 67.5 ppm of an C12 or higher amine oxide surfactant; and
   from about 1200 ppm to about 10 ppm of a chelant,
wherein the composition does not contain organic solvent and wherein the alkyl polyglycoside surfactant having a critical micelle concentration (CMC) of 1000 or more does not interfere with the biocidal activity of the quaternary ammonium compound.

10. The composition of claim 9, further comprising a primary, secondary, or tertiary amine.

11. A method of residual sanitizing for a surface comprising:
   contacting a surface, article, and/or substrate with the sanitizing composition of claim 9.

12. The method of claim 11, wherein the contacting results in inactivation and/or reduction of infectious agents on the surface, article, and/or substrate.

13. The method of claim 11, wherein the infectious agents comprise bacteria, viruses, and/or yeasts.

* * * * *

UNITED STATES PATENT AND TRADEMARK OFFICE
CERTIFICATE OF CORRECTION

PATENT NO. : 10,945,431 B2
APPLICATION NO. : 16/548558
DATED : March 16, 2021
INVENTOR(S) : Yamini Karandikar et al.

It is certified that error appears in the above-identified patent and that said Letters Patent is hereby corrected as shown below:

In the Claims

In Column 34, Claim 1, Line 34:
DELETE the second "a" before "dialkyl"

In Column 34, Claim 6, Line 56:
DELETE "Contacting" before "a"
INSERT --contacting-- before "a"

In Column 35, Claim 8, Line 4:
DELETE "claim 6," before "wherein"
INSERT --claim 7,-- before "wherein"

In Column 35, Claim 13, Line 29:
DELETE "claim 11," before "wherein"
INSERT --claim 12,-- before "wherein"

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*